United States Patent [19]

Krimmer et al.

[11] Patent Number: 4,918,223
[45] Date of Patent: Apr. 17, 1990

[54] METHOD OF PREPARING N-ACYLATED MERCAPTO-ALPHA-AMINO ACIDS

[75] Inventors: Hans-Peter Krimmer, Frankfurt; Karlheinz Drauz, Freigericht, both of Fed. Rep. of Germany

[73] Assignee: Degussa Aktiengesellschaft, Frankfurt am Main, Fed. Rep. of Germany

[21] Appl. No.: 230,028

[22] Filed: Aug. 9, 1988

[30] Foreign Application Priority Data

Aug. 21, 1987 [DE] Fed. Rep. of Germany ....... 3727897

[51] Int. Cl.$^4$ ...................... C07C 51/08; C07C 67/00; C07D 213/80; C07D 333/22
[52] U.S. Cl. .................................. 562/556; 546/318; 549/76; 560/16; 560/148; 562/426; 562/500; 562/502; 562/507; 562/557; 562/558
[58] Field of Search .................. 560/16, 148; 562/426, 562/500, 502, 507, 556, 557, 558; 549/76; 546/318

[56] References Cited

U.S. PATENT DOCUMENTS

| | | | |
|---|---|---|---|
| 3,184,505 | 5/1965 | Martin et al. ........................ | 562/557 |
| 4,370,493 | 1/1983 | Davis .................................. | 562/444 |
| 4,371,705 | 2/1983 | Davis .................................. | 562/444 |
| 4,375,555 | 3/1983 | Davis .................................. | 562/444 |

Primary Examiner—Werren B. Lone
Assistant Examiner—Vera C. Clarke
Attorney, Agent, or Firm—Cushman, Darby & Cushman

[57] ABSTRACT

N-acylated mercapto-α-amino acids of the general formula

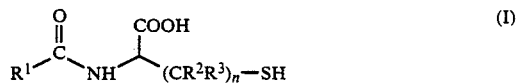

are prepared by reacting a nitrile of the general formula

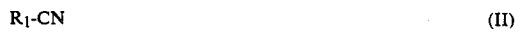

at a temperature between 0° C. and 100° C. in water or in a mixture of water and an organic solvent which is at least partially miscible with water, in the presence of a base with a mercapto-α-amino acid of the general formula

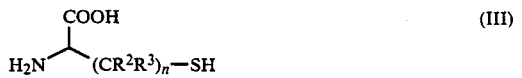

and subsequently releasing the N-acylated mercapto-α-amino acid of general formula (I) with an acid. Mercapto-α-amino acids can be selectively acylated on the amino group in this manner in a relatively simple manner.

10 Claims, No Drawings

METHOD OF PREPARING N-ACYLATED MERCAPTO-ALPHA-AMINO ACIDS

The invention relates to a method of preparing N-acylated mercapto-α-amino acids of the general formula:

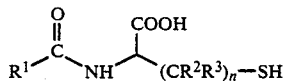

in which:

$R_1$ signifies hydrogen ($C_1$-$C_{18}$)-alkyl, linear or branched, unsubstituted or singly to triply substituted with hydroxy, ($C_1$-$C_4$)-alkoxy, aryloxy, ($C_1$-$C_4$)-alkyl mercapto, aryl mercapto, phosphono, ($C_1$-$C_4$)-alkyl phosphino, aryl phosphino, carboxy, ($C_1$-$C_4$)-alkoxy carbonyl, ($C_3$-$C_8$)-cycloalkyl, ($C_7$-$C_{12}$)-bicycloalkyl; aryl-($C_1$-$C_8$)-alkyl in which instance an unsubstituted or singly to triply substituted phenyl ring stands for aryl and the substituents can be ($C_1$-$C_8$)-alkyl, linear or branched, ($C_3$-$C_8$)cycloalkyl, ($C_2$-$C_5$)-alkenyl, ethinyl, hydroxy-($C_1$-$C_4$)-alkyl, ($C_1$-$C_4$)-alkoxy-($C_1$-$C_4$)-alkyl, mercapto- ($C_1$-$C_4$)-alkyl, ($C_1$-$C_4$)-alkyl mercapto-($C_1$-$C_4$)alkyl, carboxy-($C_1$-$C_4$)-alkyl, aryl, pyridyl, hydroxy, ($C_1$-$C_5$)-alkoxy, aryloxy, halogen, amino, mono-or di-($C_1$-$C_5$)-alkyl amino, ($C_1$-$C_4$)-acyl amino, ($C_1$-$C_4$)-alkoxy carbonyl amino, nitro, cyano, phospho, phosphono, phosphino, ($C_1$-$C_4$)acyl, carboxy, ($C_1$-$C_4$)-alkoxy carbonyl, mercapto, ($C_1$-$C_4$)-alkyl mercapto, aryl mercapto, sulfo, sulfato, sulfano and sulfino in any position to each other independently of each other; heterocyclyl-($C_1$-$C_8$)-alkyl, in which instance a mono or polycyclic, saturated or unsaturated, substituted or unsubstituted heterocyclic group with one or more heteroatoms stands for heterocyclyl in which group the substituents have the same significance, independently of each other, as defined in the case of arylalkyl; aryl, in which instance one or more substituted or unsubstituted phenyl rings condensed with each other stand for aryl, in which rings the substituents have the same significance, independently of each other, as defined in the case of aryl alkyl; heterocyclyl, in which instance a mono or polycyclic, saturated or unsaturated, substituted or unsubstituted heterocyclic group with one or more heteroatoms stands for heterocyclyl, in which group the substituents have the same meaning, independently of each other, as defined in the case of arylalkyl;

$R_2$ and $R_3$ independently of each other, represent hydrogen or ($C_1$-$C_8$)-alkyl; and n signifies a whole number from 1 to 3.

N-acylated mercapto-α-amino acids are known. They are of interest as intermediates for peptide synthesis, as active pharmaceutical substances or as cosmetic preparations. Thus, for example, N-acetyl-L-cysteine is a commercially available mucolytic agent. Furthermore, an antidotal action of N-acetyl-L-cysteine against paracetamol poisonings has been discussed more frequently in recent times. Finally, N-acetyl-L-cysteine is also used as a cosmetic preparation for the permanent deformation of human hair.

However, the selective N-acylation of mercapto-α-amino acids is difficult because of the simultaneous presence of the nucleophilic sulfhydryl group next to the amino group and is possible only with considerable effort.

SUMMARY OF THE INVENTION

The object of the present invention is to provide a method of selectively acylating mercapto-α-amino acids on the amino group in a relatively simple manner.

In accordance with the present invention, a nitrile of the general formula $$R_1\text{-CN}$$

in which $R_1$ has one of the meanings given above, is reacted with a mercapto-α-amino acid of the general formula

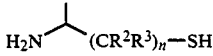

in which $R_2$ and $R_3$ have one of the indicated meanings, at a temperature between 0° C. and 100° C. in water or in a mixture of water and an organic solvent at least partially miscible with water in the presence of an organic or inorganic base and the N-acylated mercapto-α-amino acid of general formula (I) is subsequently liberated with an inorganic or organic acid.

The reaction between the nitrile of general formula (II) and the mercapto-α-amino acid of general formula (III) is preferably performed at a temperature between 50° C. and the boiling temperature of the reaction mixture.

To the extent that all reactants are water-soluble, the reaction can be performed in pure water. However, if at least one reactant is not sufficiently water-soluble, the use of an aqueous-organic reaction medium is recommended, that is, a mixture of water and an organic solvent which is at least partially miscible with water. The following can be used as organic solvent: Monovalent or polyvalent linear aliphatic, branched aliphatic, cycloaliphatic, aralphatic or aliphatic alcohols substituted by alkoxy groups such as methanol, ethanol, n-propanol, isopropanol, n-butanol, isobutanol, sec-butanol, tert-butanol, n-pentanol, n-hexanol, n-heptanol, n-octanol, cyclopentanol, cyclohexanol, benzyl alcohol, phenyl ethanol, 2-methoxyethanol, 2-ethoxyethanol, methoxyethoxyethanol, ethoxyethoxyethanol, glycol, diethylene glycol and glycerol; aliphatic or cycloaliphatic mono or polyfunctional ethers such as diethyl ether, diisopropyl ether, methyl-tert-butyl ether, tetrahydrofuran, 1,4-dioxane, 1,2-dimethoxyethane, 1,2-diethoxyethane, diethylene glycol dimethyl ether and diethylene glycol diethyl ether; carboxylic acid alkyl esters of formic acid, acetic acid, propionic acid, butyric acid, valeric acid, isobutyric acid and isovaleric acid with methyl, ethyl, n-propyl, iso-propyl, n-butyl, iso-butyl, sec-butyl, t-butyl, pentyl and hexyl alcohol, especially acetic esters (e.g. ethyl acetate); carboxylic acid amides of formic acid, acetic acid and propionic acid with ammonia, methyl amine, dimethyl amine, ethyl amine and diethyl amine, especially N,N-dimethyl formamide; cycloaliphatic lactams such as N-methyl pyrrolidone; tris-alkyl esters of phosphoric acid such as phosphoric acid trimethyl ester and phosphoric acid triethyl ester; tris-amides, tris-alkyl amides and tris-dialkyl amides of phosphoric acid such as hexamethylphosphoric acid trisamide; dialkyl sulfoxides such as dimethylsulfoxide, or dialkyl or cycloalkyl sulfones such as sulfolane; or ureas whose amino groups can be substituted with one, two, three or four aliphatic or cycloaliphatic groups such as 1,3-dimethyl-imidazoline-2-one.

The ratio between the water and the organic solvent depends on the structural conditions of the reactants to be dissolved. The solvent is preferably water alone or a mixture in which the ratio is water : organic solvent =1:20 (v/v). Mixtures which have proven themselves quite useful are those consisting of water and methanol or isopropanol, in each instance in a ratio of 1:3 (v/v).

The reaction between the nitrile of general formula (II) and the mercapto-α-amino acid of general formula (III) also requires the presence of an organic or inorganic base. Suitable bases are e.g. alkali metal hydroxides or alkaline earth metal hydroxides such as lithium hydroxide, sodium hydroxide, potassium hydroxide, magnesium hydroxide and calcium hydroxide; alkali metal carbonates or alkaline earth metal carbonates or hydrogen carbonates such as lithium carbonate, sodium carbonate, potassium carbonate, magnesium carbonate and calcium carbonate or hydrogen carbonate; amines such as ammonia, alkyl amines, dialkyl amines or trialkyl amines, e.g. methyl, ethyl, propyl, iso-propyl, n-butyl, iso-butyl, sec-butyl, tert-butyl, dimethyl, diethyl, di-n-propyl, di-iso-propyl, di-n-butyl, di-iso-butyl, di-sec-butyl, trimethyl, triethyl, tri-n-propyl, diisopropylmethyl and diisopropylethyl amine; or unsaturated organic heterocyclic nitrogenous bases, e.g. pyridine, α-, β- or τ-picoline, lutidine, quinoline, isoquinoline, collidine, pyrollidine, piperidine, piperazine, N-methylpiperidine and quinuclidine. Especially preferred bases are sodium hydroxide, potassium carbonate and ammonia. The base is advantageously added in such an amount that the pH of the reaction mixture is between pH 6 and pH 14, preferably between pH 8 and pH 10.

It is advantageous to perform the reaction between the nitrile of general formula (II) and the mercapto-α-amino acid of general formula (III) under an inert atmosphere (e.g. nitrogen) in order to minimize the risk of oxidizing the mercapto compound to the corresponding disulfide. It is especially advantageous to pass nitrogen through the reaction mixture during the entire reaction in order to simultaneously expel the ammonia being produced, which can shorten the reaction time required. A reaction time between 30 minutes and 48 hours is necessary, depending on the reactants used. However, a reaction time up to 8 hours is generally sufficient.

Ammonia develops during the reaction which can be adsorbed by a gas wash with water and used in a further charge as base. After the reaction is ended, the reaction mixture must be treated with an inorganic or organic acid in order to liberate the N-acylated mercapto-α-amino acid of the general formula (I). Suitable acids are e.g. hydrohalic acids such as hydrochloric acid, hydrobromic acid and hydroiodic acid, sulfuric acid, nitric acid, phosphoric acid or carbon dioxide as well as mono or polyfunctional organic carboxylic acids, especially formic acid, acetic acid and propionic acid. The acid is advantageously added in such an amount that the pH of the reaction mixture is between pH 1 and pH 7, preferably between pH 2 and pH 5.

It can be advantageous, in those instances in which an aqueous-organic reaction medium must be used but the N-acylated mercapto-α-amino acid of general formula (I) formed is readily soluble in the mixture, to distill off the solvent or solvents, advantageously under reduced pressure, before the addition of the acid and to take up the residue in pure water. The product then precipitates during acidification of the aqueous solution, usually in reagent purity.

In other instances it is necessary, in order to liberate the N-acylated mercapto-α-amino acid of the general formula (I), to heat the reaction mixture after addition of the acid, for 15 minutes to 10 hours, preferably up to 3 hours, to a temperature between 40° C. and 100° C., especially between 70° C. and the boiling temperature of the reaction mixture. Then the product is usually separated in pure form during cooling.

The process of the present invention has the advantage in the reaction of chiral, that is, optically active mercapto-α-amino acids of general formula (III) that no racemization takes place.

DETAILED DESCRIPTION OF PREFERRED EMBODIMENTS

The invention is illustrated in more detail in the following examples:

Example 1:

N-nicotinoyl-D,L-cysteine 41.6 g (0.4 mole) nicotinic acid nitrile, 70.5 g (0.4 mole) D,L-cysteine hydrochloride monohydrate and 55.2 g (0.4 mole) potassium carbonate were heated in 500 ml methanol and 500 ml water for 6 hours at the boiling point. Then, the solvent was removed under reduced pressure, the residue taken up in 300 ml water, adjusted with concentrated hydrochloric acid to pH 5 and heated 45 minutes at the boiling point. After the mixture cooled off, 78.7 g (87% of theory) colorless product with a melting point of 195° C. were recovered by suction.

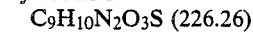

Calculated: C 47.78%; H 4.45%; N 12.38%; S 14.17%;

Found: 47.72%; 4.50%; 12.17%; 14.19%; $^1$H-NMR (DMSO-d$^6$): δ=2.64 (t; 1H, SH), 2.97 (m; 2H, β-CH$_2$), 4.49 (m; 1H, α-H), 7.55 (dd; 1H, 5'-H), 8.24 (d; 1H, 4'-H), 8.76 (d; 1H, 6'H), 8.91 (d; 1H, NH), 9.05 (s: 1H, 2'-H), 13 (wide; 1H, COOH).

Example 2:

N-nicotinoyl-D-penicillamine-hydrochloride 20.8 g (0.2 mole) nicotinic acid nitrile, 29.8 g (0.2 mole) D-penicillamine and 13.8 g (0.1 mole) potassium carbonate were heated in 350 ml methanol and 150 ml water for 6 hours at the boiling point. The mixture was acidified with concentrated hydrochloric acid to pH 4 and heated 45 minutes at the boiling point. After the mixture cooled off, 36.5 g (63% of theory) of the product precipitated as hydrochloride with a melting point of 164° C. $[α]^{25}_D$= +4.0° (c=2 in 1N NaOH)

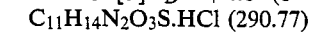

Calculated: C 45.44%; H 5.20%; N 9.63%; S 11.03%;

Found: 45.27%; H5.20%; 9.29%; 11.14%; $^1$H-NMR (DMSO-d$^6$): δ=1.52 (s; 6H, 2 CH$_3$), 3.20 (s; 1H SH), 4.72 (d; 1H, α-H), 7.55 (dd; 1H, 5'-H), 8.26 (dt; 1H, 4'-H), 8.64 (d; 1H, NH), 8.75 (m; 1H, 6'-H), 9.04 (d; 1H, 2'-H), 12.9 (wide; 1H, COOH).

Example 3:

N-(4'-chlorobenzoyl)-D-penicillamine 27.5 g (0.2 mole) 4-chlorobenzonitrile, 29.8 g (0.2 mole) D-penicillamine and 13.8 g (0.1 mole) potassium carbonate were heated in 350 ml methanol and 150 ml water for 6 hours at the boiling point. After the mixture was acidified with concentrated hydrochloric acid to pH 4, it was heated one hour under nitrogen at the boiling point. After it cooled off, 42.6 g (74% of theory) of a colorless precipitate was isolated, which had a melting point of 174° C.

$C_{12}H_{14}ClNO_3S$ (287.76)

Calculated: C 50.09%; H 4.91%; Cl 12.32%; N 4.87%; S 11.14%;

Found: 50.27%; 4.99%; 12.16%; 4.69%; 11.10%;

$^1$H-NMR (DMSO-d$^6$): δ=1.57 (s; 6H, 2CH$_3$), 3.20 (s; 1H, SH), 4.68 (d; 1H, α-H), 7.56 (d; 2H, phenyl), 8.02 (d; 2H, phenyl), 8.52 (d; 1H, NH), 13 (wide; 1H, COOH).

Example 4

N-(4'-bromobenzoyl)-D-penicillamine 36.4 g (0.2 mole) 4-bromobenzonitrile, 29.8 g (0.2 mole) D-penicillamine and 13.8 g (0.1 mole) potassium carbonate were heated in 350 ml methanol and 150 ml water for 6 hours at the boiling point. After the mixture was acidified with concentrated hydrochloric acid to pH 4, it was heated one hour to a boil. After it cooled off, 53.6 g (81% of theory) of the product were isolated as a colorless precipitate with a melting point of 176° C.

$C_{12}H_{14}BrNO_3S$ (332.22)

Calculated: C 43.38 %; H 4.25 %; Br 24.05 %; N 4.22 %; S 9.65 %;

Found: 43.27 %; 4.44 %; 23.91 %; 4.36 %; 9.19 %;

$^1$H-NMR (DMSO-d$^6$): δ=1.57 (s; 6H, 2 CH$_3$), 3.18 (s; 1H, SH), 4.67 (d; 1H, α-H), 7.70 (d; 2H, phenyl), 7.85 (d; 2H, phenyl), 8.52 (d; 1H, NH), 12.92 (wide; 1H, COOH).

Example 5:

N-phenacetyl-L-cysteine-monohydrate 117.2 g (1 mole) benzyl cyanide, 176.2 g (1 mole) L-cysteine hydrochloride monohydrate and 138 g (1 mole) potassium carbonate were heated in 1700 ml methanol and 750 ml water for 8 hours under nitrogen at the boiling point. The solvent was concentrated by evaporation under reduced pressure to 800 ml and the residue acidified with concentrated hydrochloric acid to pH 4. 238 g (93% of theory) of the product was recovered as monohydrate. It had a melting point of 105°–108° C.

$[α]^{25}_D = -24.7°$ (c=2 in 1N NaOH)

$C_{11}H_{13}NO_3S \cdot H_2O$ (257.30)

Calculated: C 51.34%; H 5.87%; N 5.44%;

Found: 51.86%; 5.43%; 5.02%;

$^1$H-NMR (DMSO-d$^6$): δ=2.80 (m; 2H, β-CH$_2$) 3.48 (s; 1H, SH), 3.55 (s; 2H, benzyl-CH$_2$), 4.41 (mc; 1H, α-H), 7.30 (mc; 5H, phenyl), 8.42 (d; 1H, NH), 13 (wide; 1H, COOH).

Example 6:

N-(4'-methylohenacetyl)-D,L-cysteine 26.2 g (0.2 mole) 4-tolyl acetonitrile, 35.2 g (0.2 mole) D,L-cysteine hydrochloride monohydrate and 27.6 g (0.2 mole) potassium carbonate were heated in 350 ml methanol and 250 ml water for 6 hours at the boiling point. Then the solvent was removed under reduced pressure, the residue taken up in 200 ml water and adjusted with concentrated hydrochloric acid to pH 4. 40.8 g (81% of theory) colorless product with a melting point of 123° C. precipitated.

$C_{12}H_{15}NO_3S$ (253.32)

Calculated: C 56.89%; H 5.96%; N 5.53%; S 12.67%;

Found: 56.73%; 5.76%; 5.26%; 12.32%;

$^1$H-NMR (DMSO-d$^6$): δ=2.28 (s; 3H, 4'-CH$_3$), 2.37 (wide t; 1H, SH), 2.79 (m; 2H, β-CH$_2$), 3.44 (s; 2H, benzyl-CH$_2$), 4.37 (m; 1H, α-H), 7.13 (mc; 4H, phenyl), 8.36 (d; 1H, NH), 12.8 (wide; 1H, COOH).

Example 7:

N-(3',5'-dimethylphenacetyl)-D,L-cysteine 29.0 g (0.2 mole) 3,5-dimethylbenzylcyanide, 35.2 g (0.2 mole) D,L-cysteine hydrochloride monohydrate and 27.6 g 0.2 mole) potassium carbonate were heated in 500 ml methanol and 250 ml water for 6 hours at the boiling point. Then the solvent was removed under reduced pressure, the residue taken up in 200 ml water and adjusted with concentrated hydrochloric acid to pH 4. 41.8 g (78% of theory) colorless product with a melting point of 135 C precipitated as colorless crystals.

$C_{13}H_{17}NP_3S$ (267.35)

Calculated: C 58.40%; H 6.41%; N 5.24%; S 11.99%;

Found: 58.44%; 6.26%; 5.34%; 12.21%;

$^1$H-NMR (DMSO-d$^6$): δ=2.22 (s; 6H, 3',5'-CH$_3$), 2.39 (t; 1H, SH), 2.82 (m; 2H, β-CH$_2$), 3.46 (s; 2H, benzyl-CH$_2$), 4.40 (m; 1H, α-H), 6.82 (s; 1H, 4'-H), 6.90 (s; 2H, 2',6'-H), 8.38 (d; 1H, NH), 12.8 (wide; 1H, COOH).

Example 8:

N-(4'-fluorophenacetyl)-L-cysteine monohydrate 27.0 g (0.2 mole) 4-fluorobenzyl cyanide, 35.2 g (0.2 mole) L-cysteine hydrochloride monohydrate and 27.6 g (0.2 mole) potassium carbonate were heated in 350 ml methanol and 150 ml water for 8 hours at the boiling point. The solvent was removed under reduced pressure, the residue taken up in 150 ml water and acidified with concentrated hydrochloric acid to pH 4. In this manner, 33.6 g (61% of theory) product were obtained as hydrate with a melting point of 115° C.

$[α]^{25}_D = -33.8°$ (c=2 in 1N NaOH).

$C_{11}H_{12}FNO_3S \cdot H_2O$ (275.29)

Calculated: C 47.99%; H 5.13%; N 5.09%; S 11.66%;

Found: 48.24%; 4.95%; 5.23%; 11.06%;

$^1$H-NMR (DMSO-d$^6$): δ=2.81 (m; 2H, β-CH$_2$), 3.48 (s; 1H, SH), 3.52 (s; 2H, benzyl-CH$_2$), 4.34 (mc; 1H, α-H), 7.12 (mc; 2H, phenyl), 7.31 (mc; 2H, phenyl), 8.32 (d; 1H, NH), 12.95 (wide; 1H, COOH).

Example 9:

N-(2',4'-dichlorophenacetyl)-D,L-cysteine 37.2 g (0.2 mole) 2,4-dichlorobenzyl cyanide, 35.2 g (0.2 mole) D,L-cysteine hydrochloride monohydrate and 15.8 g (0.2 mole) pyridine were heated in 500 ml 1,4-dioxane and 300 ml water for 8 hours to 80° C. Then the solvent was removed under reduced pressure, the residue taken up in 300 ml water and acidified with concentrated hydrochloric acid to pH 3. 51.1 g (83% of theory) colorless product with a melting point of 164°–165° C. were obtained.

$C_{11}H_{11}Cl_2NO_3S$ (308.18)

Calculated: C 42.87%; H 3.57%; 4.55%; S 10.40%; Cl 23.01%;

Found: 42.50%; 3.56%; 4.76%; 10.18%; 23.28%;

Example 10:

N-(2'-thienylacetyl)-D,L-cysteine 24.6 g (0.2 mole) thiophene-2-acetonitrile, 35.2 g (0.2 mole) D,L-cysteine hydrochloride monohydrate and 27.6 g (0.2 mole) potassium carbonate were heated in 500 ml methanol and 250 ml water for 6 hours at the boiling point. Then the solvent was removed under reduced pressure, the residue taken up in 200 ml water and adjusted with concentrated hydrochloric acid to pH 4. 40.8 g (83% of theory) colorless product with a melting point of 138°–140° C. precipitated.

C$_9$H$_{11}$NO$_3$S$_2$ (245.32)

Calculated: C 44.06%; H 4.52%; N 5.71%; S 26.14%;
Found: 44.23%; 4.30%; 5.61%; 26.21%;

$^1$H-NMR (DMSO-d$^6$): δ=2.25 (wide; 1H, SH), 2.82 (m; 2H, β-CH$_2$), 3.74 (s; 2H, benzyl-CH$_2$), 4.43 (m; 1H, α-H), 6.96 (mc; 2H, 3',4'-H), 7.36 (dd; 1H, 5'H), 8.43 (d; 1H, NH), 12.9 (wide; 1H, COOH).

Example 11:

N-(3'-thienylacetyl)-D,L-cysteine 24.6 g (0.2 mole) thiophene-3-acetonitrile, 35.2 g (0.2 mole) D,L-cysteine hydrochloride monohydrate and 20.2 g (0.2 mole) triethyl amine were heated in 150 ml isopropanol and 150 ml water for 4 hours at the boiling point. Then the solvent was removed under reduced pressure, the residue taken up in 250 ml water and acidified with semi-concentrated sulfuric acid to pH 4. 40.8 g (83% of theory) colorless product with a melting point of 125°–126° C. were obtained.

C$_9$H$_{11}$NO$_3$S$_2$ (245.32)

Calculated: C 44.06%; H 4.52%; N 5.71%; S 26.14%;
Found: 44.26%; 4.31%; 5.77%; 26.57%;

$^1$H-NMR (DMSO-d$^6$): δ=2.40 (wide t; 1H, SH), 2.80 (m; 2H, β-CH$_2$), 3.52 (s; 2H, benzyl-CH$_2$), 4.41 (m; 1H, α-H), 7.06 (d; 1H, 4'-H), 7.28 (d; 1H, 2'-H), 7.45 (dd; 1H, 5'-H), 8.41 (d; 1H, NH), 12.9 (wide; 1H, COOH).

Example 12:

N-(4'-fluorophenacetyl)-D-penicillamine 27.0 g (0.2 mole) 4-fluorobenzyl cyanide, 29.8 g (0.2 mole) D-penicillamine and 13.8 g (0.1 mole) potassium carbonate were heated in 350 ml methanol and 150 ml water for 6 hours at the boiling point. Then the solvent was removed under reduced pressure, the residue taken up in 200 ml water and acidified with concentrated hydrochloric acid to pH 4. 33.5 g (59% of theory) of the precipitated product were isolated, which exhibited a melting point of 130° C. after drying.

C$_{13}$H$_{16}$FNO$_3$S (285.34)

Calculated: C 54.72%; H 5.65%; N 4.91%; S 11.23%;
Found: 54.79%; 5.48%; 5.34%; 11.19%;

$^1$H-NMR (DMSO-d$^6$): δ=1.32 (s; 3H, CH$_3$), 1.37 (S; 3H, CH$_3$) 3.33 (wide; 1H, SH), 3.59 (dd; 2H, CH$_2$), 4.41 (d; 1H, α-H), 7.10 (mc; 2H, phenyl), 7.30 (mc; 2H, phenyl), 8.30 (d; 1H, NH), 12.8 (wide; 1H, COOH).

Example 13:

N-(4'-hydroxyphenacetyl)-D-penicillamine 26.6 g (0.2 mole) 4-hydroxybenzyl cyanide, 29.8 g (0.2 mole) D-penicillamine and 13.8 g (0.1 mole) potassium carbonate were heated in 350 ml methanol and 150 ml water for 6 hours at the boiling point. When the mixture was acidified with concentrated hydrochloric acid to pH 4, 28.9 g (51% of theory) of product with a melting point of 157° C. precipitated.

[α]$^{25}_D$=+13.0° (c=2 in 1 N NaOH).

C$_{13}$H$_{17}$NO$_4$S (283.34)

$^1$H-NMR (DMSO-d$^6$): δ=1.36 (s; 3H, CH$_3$), 1.39 (s; 3H, CH$_3$), 3.42 (dd; 2H, CH$_2$), 3.60 (wide; 1H, SH), 4.40 (d; 1H, α-H), 6.69 (d; 2H, phenyl), 7.08 (d; 2H, phenyl), 8.11 (d; 1H, NH), 9.40 (wide; 1H, 4'-OH), 13 (wide; 1H, COOH).

Example 14:

N-(2'-pyridoyl)-D-penicillamine 20.8 g (0.2 mole) picolinic acid nitrile, 29.8 g (0.2 mole) D-penicillamine and 13.8 g (0.1 mole) potassium carbonate were heated in 350 ml methanol and 150 ml water for 6 hours at the boiling point. Then the solvent was removed under reduced pressure, the residue taken up in 200 ml water and acidified with concentrated hydrochloric acid to pH 5. 32.0 g (63% of theory) colorless product with a melting point of 150°–152° precipitated.

C$_{11}$H$_{14}$N$_2$O$_2$S (254.31)

$^1$H-NMR (DMSO-d$^6$): δ=1.40 (s; 3H, CH$_3$), 1.53 (s; 3H, CH$_3$), 3.32 (wide; 1H, SH), 4.58 (d; 1H, α-H), 7.68 (m; 1H, pyridine-H), 8.09 (m; 2H, pyridine-H), 8.74 (m; 2H, pyridine-H and NH), 13.2 (wide; 1H, COOH).

Example 15:

N-isonicotinoyl-D-penicillamine semihydrate 20.8 g (0.2 mole) isonicotinic acid nitrile, 29.8 g (0.2 mole) D-penicillamine and 13.8 g (0.1 mole) potassium carbonate were heated in 350 ml methanol and 150 ml water for 6 hours at the boiling point. The solvent was removed under reduced pressure, the residue taken up in 200 ml water and adjusted with concentrated hydrochloric acid to pH 5. 37.1 g (70% of theory) colorless product precipitated as semihydrate with a melting point of 200°–202° C.

[α]$^{25}_D$=+2.5. (c=2 in 1N NaOH).

C$_{11}$H$_{14}$N$_2$O$_3$S . ½ H$_2$O (263.32)

Calculated: C 50.18%; H 5.74%; N 10.64%; S 12.18%;
Found: 49.37%; 5.69%; 10.81%; 11.90%;

$^1$H-NMR (DMSO-d$^6$): δ=1.48 (s: 6H, 2CH$_3$), 3.22 (s; 1H, SH), 4.69 (d; 1H, α-H), 7.80 (d; 2H, pyridine-', 5'-H), 8.68 (d; 1H, NH), 8.73 (d; 2H, pyridine-2', 6'-H), 12.9 (wide; 1H, COOH).

Example 16:

N-acetyl-L-cysteine 12.3 g (0.3 mole) acetonitrile were heated in 250 ml water for one hour at the boiling point while passing nitrogen through. Then the mixture was cooled to 60° C. and 4.4 g (0.11 mole) sodium hydroxide and subsequently 12.1 g (0.1 mole) L-cysteine were added.

The reaction mixture was heated for 5 hours under reflux at the boiling point while gently passing nitrogen through.

Then all volatile components of the reaction mixture were evaporated under reduced pressure. The remaining oil was taken up in 10 ml water and acidified with concentrated hydrochloric acid to pH 3. As the mixture was cooled down to 0.C, sodium chloride precipitated, which was filtered off.

11.5 g (71% of theory) product crystallized out of the filtrate as colorless needles with a melting point of 108°–110° C.

[α]$^{25}_D$=+4.4 (c=2; H$_2$O)

Example 17:

N-butanoyl-L-cysteine 12.1 g (0.1 mole) L-cysteine, 6.9 g (0.1 mole) butyronitrile and 6.9 g (0.05 mole) potassium carbonate were heated in 150 ml methanol and 80 ml water for 12 hours to a boil while passing nitrogen through. Then all volatile components of the reaction mixture were evaporated under reduced pressure.

The residue was adjusted with concentrated hydrochloric acid to pH 4 and digested with 100 ml acetone. As a result, the potassium chloride, which had formed, precipitated. After removal by suction, the filtrate was condensed by evaporation in a vacuum, the residue taken up in 100 ml water and extracted three times with 50 ml dichloromethane per extraction in order to remove excess organic components. The aqueous phase was condensed by evaporation under reduced pressure. 11.5 g (60% of theory) product were obtained as bright yellow oil.

Decomposition occurred during an attempt to purify the oil by distillation. Attempts at crystallization were also unsuccessful.

F. Nome and J. Feuchler likewise describe N-butanoyl-L-cysteine as an oil in a paper in JACS 99 1554 (1977) without indicating any physical properties. This paper describes reacting this product to make other products.

Therefore, the oil was taken up in 20 ml isopropanol for characterization and gaseous ammonia introduced. The N-butanoyl-L-cysteine ammonium salt precipitated as colorless crystals with a melting point of 136°–139° C.

$[\alpha]^{20}_D = +2.9$ (c=5, H$_2$O)

C$_7$H$_{16}$N$_2$O$_3$S (208.21)

Calculated: C 40.38%; H 7.75%; N 13.45%; S 15.40%;

Found: 40.19%; 7.61%; 13.80%; 15.07%;

$^1$H-NMR (DMSO-d$^6$): $\delta$=0.85 (t; 3H, CH$_3$), 1.50 (sextet; 2H, CH$_3$-CH$_2$), 2.11 (t; 2H, CH$_2$-CO), 2.81 (ddd; 2H, CH$_2$-S), 4.04 (mc; 1H, CH), 5.6 - 7.2 (wide; 5H, NH$_4$+ and SH), 7.42 (d; 1H, NH).

Example 18:

N-[3'-(methoxycarbonyl)-propanoyl]-L-cysteine 6.7 g (0.059 mole) 3-cyano-propionic acid methylester, 7.2 g (0.059 mole) L-cysteine and 5.4 g (0.08 mole) 25% aqueous ammonia were heated in 90 ml methanol and 45 ml water for 4 hours at the boiling point while passing nitrogen through. Then all volatile components of the reaction mixture were evaporated under reduced pressure. The oily residue was acidified with concentrated hydrochloric acid to pH 4 and subsequently digested with 100 ml acetone, causing ammonium chloride to be precipitated. After filtering, the filtrate was concentrated by evaporation in a vacuum, and the residue was taken up in 100 ml water.

The aqueous solution was extracted three times with 50 ml dichloromethane per extraction, in order to remove excess organic components. The aqueous phase was concentrated by evaporation under reduced pressure. 11.5 g (83% of theory) product were obtained as colorless oil.

Attempts at distillation resulted in decomposition.

$^1$H-NMR (DMSO-d$^6$) $\delta$=2.25 - 2.50 (m; 4 H, CH$_2$-CH$_2$), 2.79 (ddd; 2 H, CH$_2$-S), 3.57 (s; 3 H, COOCH$_3$), 4.08 (mc; 1 H, CH), 7.62 (d; 1H, NH), 10.8 (wide; 1 H, COOH).

What is claimed is:

1. A method of preparing N-acylated mercapto-α-amino acids of the formula

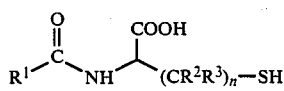

(I)

in which:

R$_1$ signifies hydrogen, (C$_1$-C$_{18}$)-alkyl, linear or branched, unsubstituted or singly to triply substituted with aryl mercapto, (C$_1$-C$_4$)-alkoxy carbonyl; aryl-(C$_1$-C$_8$)-alkyl in which instance an unsubstituted or singly to triply substituted phenyl ring stands for aryl and the substituents can be (C$_1$-C$_8$)-alkyl, linear or branched, (C$_1$-C$_4$)-alkoxy-(C$_1$-C$_4$)-alkyl, aryl, pyridiyl, hydroxy, (C$_1$-C$_4$)-alkoxy, aryl oxy, halogen, amino, mono- or di-(C$_1$-C$_5$)-alkyl amino, (C$_1$-C$_4$)-acyl amino, (C$_1$-C$_4$)-alkoxy carbonyl amino, nitro, carboxy, (C$_1$-C$_4$)-alkoxy carbonyl, (C$_1$-C$_4$)-alkyl mercapto, and aryl mercapto in any position to each other independently of each other; thienylmethyl; aryl, in which instance one or more substituted or unsubstituted phenyl rings condensed with each other stand for aryl, in which rings the substituents have the same significance, independently of each other, as defined in the case of arylalkyl; or pyridinyl-2, pyridinyl-3, pyridinyl-4, thienyl-2, thienyl-3;

R$_2$ and R$_3$ independently of each other, represent hydrogen or (C$_1$-C$_8$)-alkyl; and n signifies a whole number from 1 to 3 which comprises reacting a nitrile of the general formula:

(II)

in which R$_1$ has the meaning given above with a mercapto-α-amino acid of the general formula:

(III)

in which R$_2$ and R$_3$ have the meanings given above, at a temperature between 0° C. and 100° C. in water or in a mixture of water and an organic solvent which is at least partially miscible with water, in the presence of an organic or inorganic base.

2. A method as set forth in claim 1 in which the base is added in such an amount that the pH of the reaction mixture is between pH 6 and pH 14.

3. A method as set forth in claim 1 or claim 2 in which the reaction is performed under an inert gas atmosphere.

4. A method as set forth in claim 3 in which the inert gas is nitrogen.

5. A method as set forth in claim 5 in which the nitrogen is passed through the reaction mixture during the reaction.

6. A method as set forth in claim 1 including the step of liberating the N-acylated mercapto-α-amino acid of general formula (I) with an inorganic or organic acid.

7. A method as set forth in claim 6 in which the solvent or solvents are distilled off and the residue taken up in water before the acid is added.

8. A method as set forth in claim 6 or claim 7 in which the reaction mixture is heated to a temperature between 40° C. and 100° C. after the addition of the acid.

9. A method as set forth in claim 6 or claim 7 in which the acid is added in such an amount that the pH of the reaction mixture is between pH 1 and pH 7.

10. A method as set forth in claim 1 or claim 6 in which the mercapto-o-aminoacid is selected from the group consisting of penicillamine and cysteine.

* * * * *